United States Patent [19]

Isaacson et al.

[11] Patent Number: 5,381,333
[45] Date of Patent: Jan. 10, 1995

[54] CURRENT PATTERNS FOR ELECTRICAL IMPEDANCE TOMOGRAPHY

[75] Inventors: David Isaacson, Latham; Jonathan C. Newell, Glenmont; David G. Gisser, Albany, all of N.Y.

[73] Assignee: Rensselaer Polytechnic Institute, Troy, N.Y.

[21] Appl. No.: 734,591

[22] Filed: Jul. 23, 1991

[51] Int. Cl.⁶ .............................................. A61B 5/05
[52] U.S. Cl. ........................ 364/413.13; 128/734
[58] Field of Search .............. 128/734; 364/413.02, 364/413.13, 413.15

[56] References Cited

U.S. PATENT DOCUMENTS

| | | | |
|---|---|---|---|
| 4,486,835 | 12/1984 | Bai et al. | |
| 4,539,640 | 9/1985 | Fry et al. | 364/413.13 |
| 4,814,690 | 3/1989 | Melcher et al. | 324/674 |
| 4,920,490 | 4/1990 | Isaacson | 364/413.13 |

OTHER PUBLICATIONS

Isaacson; "Distinguishability of Conductivities by Electric Current Computed Tomography"; IEEE Transactions on Medical Imaging, vol. MI-5, No. 2, Jun. 1986.
Isaacson et al.; "Effects of measurement precision and finite numbers of electrodes on linear impedance imaging algorithms", Rensselaer Polytechnic Inst.; SIAM Journal on Applied Mathematics vol. 51 No. 6 Dec. 1991 pp. 1705-1731; Dialog #03420603.
Gisser et al., "Current Topics in Impedance Imaging"; Clin Phys Physiol Meas vol. 8 Suppl A 1987, Com of the Eur Communities COMAC-BME Workshop on Electr Impedance Tomogr-Appl Potential Tomogr, Sheffield, Engl, Jul. 2-4 1986 pp. 39-46; 1987; Dialog #02293207.

Primary Examiner—Gail O. Hayes
Assistant Examiner—Stephen R. Tkacs
Attorney, Agent, or Firm—Notaro & Michalos

[57] ABSTRACT

A method in electrical impedance tomography uses an adaptive repeated series of calculations and measurements to determine the best current pattern for a body having an initially unknown internal conductivity, for producing the best electrical impedance image for the body. Initially, an arbitrary current pattern and conductivity is utilized to generate a voltage pattern which is measured and compared with the theoretical voltage pattern based on the arbitrary conductivity and current patterns. When both the current pattern and the conductivity yielded by the process closely match values derived by measurements, the voltage pattern is used to produce the image.

1 Claim, 2 Drawing Sheets

CURRENT PATTERNS FOR ELECTRICAL IMPEDANCE TOMOGRAPHY

STATEMENT OF GOVERNMENT INTEREST

This invention was made in part with Government support under National Science Foundation Grants No. DMS-8603957 and EET-8706340, and National Institutes of Health Grant No. GM-39388. The Government has certain rights in this invention.

FIELD AND BACKGROUND OF THE INVENTION

The present invention relates in general to electrical impedance tomography, and in particular to a new and useful method and apparatus for the adaptive selection and application of optimal current patterns for use in electric current computed tomography (ECCT) to reconstruct the best image.

An apparatus for practicing electric current tomography comprising 32 electrodes and a plurality of current generators is disclosed in an article by the coinventors of the present invention, entitled "An Electric Current Tomograph", IEEE TRANSACTIONS ON BIOMEDICAL ENGINEERING, Vol. 35, No. 10, October 1988.

A process and apparatus for utilizing a similar array of electrodes in computed tomography is disclosed in U.S. Pat. No. 4,920,490 granted to one of the coinventors of the present invention. U.S. Pat. No. 4,920,490 is incorporated here by reference and discloses a means for distinguishing one conductivity from another. It does not disclose an adaptive process which creates the best current patterns and then uses these current patterns iteratively to reconstruct the best image.

ECCT is used to determine electrical impedance distribution within a body from electrical measurements made on the surface of the body. It has a wide range of possible applications in medical imaging, geology and mineral exploration, in the nondestructive evaluation of solid materials, and in the control of manufacturing processes.

When many electrodes are used to make the electrical measurements at the surface of the body, as in the foregoing references, many different current patterns can be utilized. The present invention as will be explained later in this disclosure, involves a new process for determining all of the current patterns to be used, and a related process for making an image of the internal impedance distribution.

Other approaches to the selection of current patterns are disclosed in U.S. Pat. No. 4,486,835 to Bai, et al. and U.S. Pat. No. 4,539,640 to Fry, et al. Neither of these references, however, disclose the adaptive selection of optimal current patterns as in the present invention.

SUMMARY OF THE INVENTION

The method and apparatus of the present invention insures that the current patterns to be applied to the electrodes will contain the maximal amount of information about the internal impedance distribution of the body being imaged. Previous systems have used current patterns which were chosen in advanced, such as spacial impulses or spacial sinusoidal functions. The optimal current patterns however, depend on the internal impedance distribution. For this reason, the present invention finds the optimal patterns in an adaptive way which rapidly converges on an orthogonal set of basic functions.

A second feature of the present invention involves a process for finding the distribution of unknown impedance values inside an object or patient by an iterative method which involves first finding the optimal current patterns for the case where the internal impedance distribution is only a guess, than finding a new distribution based on voltages measured using those optimal current patterns. This distribution is closer to the actual one than the first, but if the process is repeated, using this distribution to find a new set of optimal patterns followed by the calculation of a third impedance distribution, etc, until reasonable convergence is reached. the result is an optimal (in the least squares sense) impedance distribution, that can be displayed as one or more images, found with an optimal set of current patterns for that distribution.

A third feature of the present invention involves a process for simultaneously producing the optimal current patterns and optimal images of the impedance distribution inside the body. To this end, an image is initially constructed which is based upon an arbitrary current pattern. From this image a better current pattern is calculated and applied to the body. The resulting voltages are measured and used to construct an improved image. This process is repeated until the current patterns converge to the optimal pattern, and at the same time, the image converges to one which is best in a least squares sense.

The present invention can be used in any system which obtains information about an internal impedance distribution by means of boundary measurements of voltages and currents or their analogs. This can be used in geologic exploration, in nondestructive evaluation of solid materials (in order to detect flaws such as cracks in pipes or other structural elements), in manufacturing process control (to determine in a nonevasive manner, whether some reaction has gone to completion for example), and in medical imaging. Possible medical applications include imaging structures in the thorax, detection of water in the lungs, detection of deep venous clots, studies of emptying of the stomach, detection of bleeding into the brain of premature newborn infants, and measurements of cardiac output. This list is not meant to be comprehensive but only provides examples where the present invention can be applied.

The present invention also advances the broader object of developing an inexpensive, light-weight clinical instrument with the ability to produce useful information from patients at much less cost, risk and inconvenience than existing high-resolution systems.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
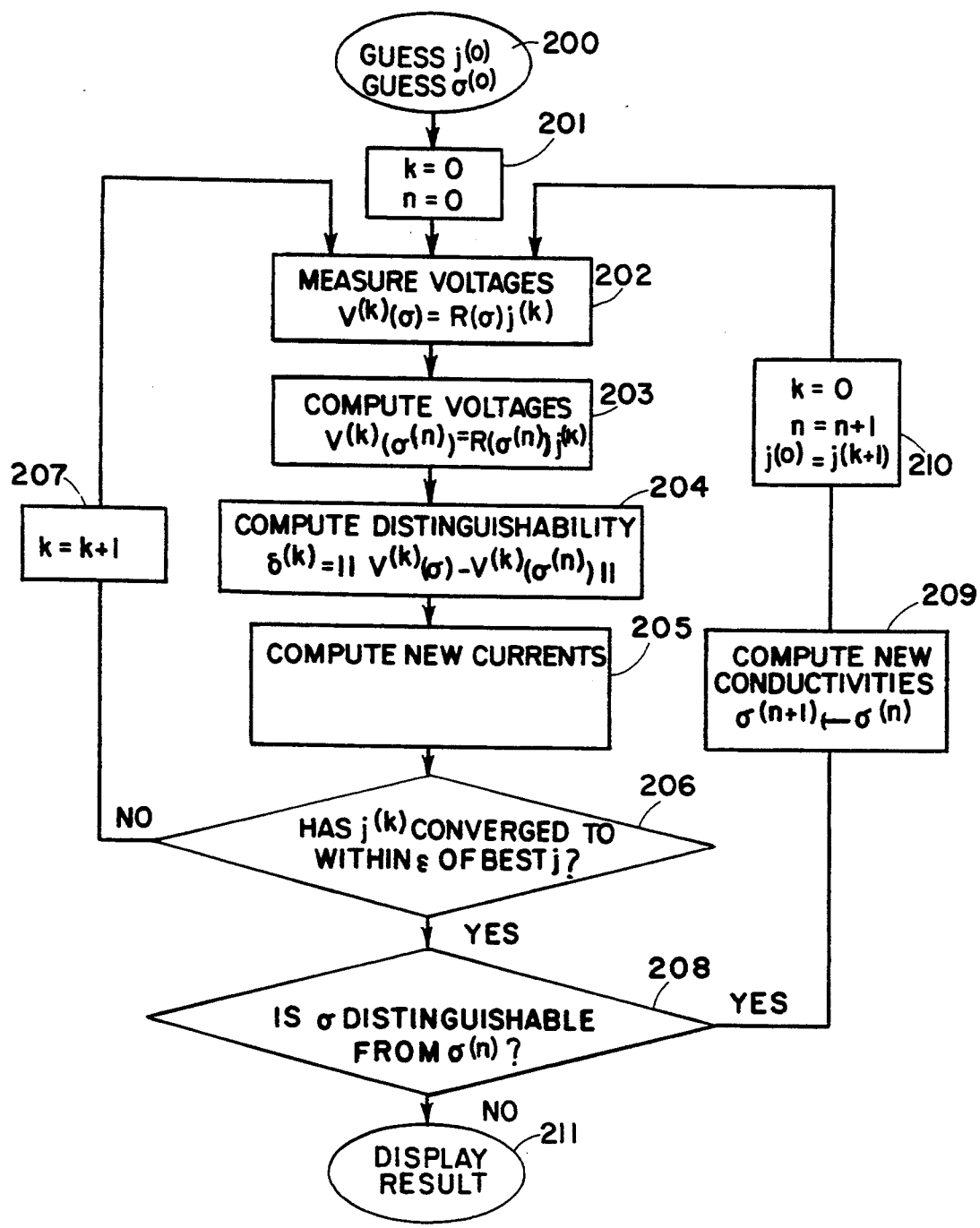
FIG. 1 is a flow chart showing the adaptive current pattern selection and adaptive conductivity distribution method of the present invention.

FIG. 1 is a flow chart showing the process of the present invention. Although the process and flow chart is similar to that disclosed in U.S. Pat. No. 4,920,490, the present invention takes the process further and into the realm of actually forming an improved image for a body whose internal impedance distribution was not initially known. FIG. 1 will be explained in greater detail later in this disclosure.

Figure 2:
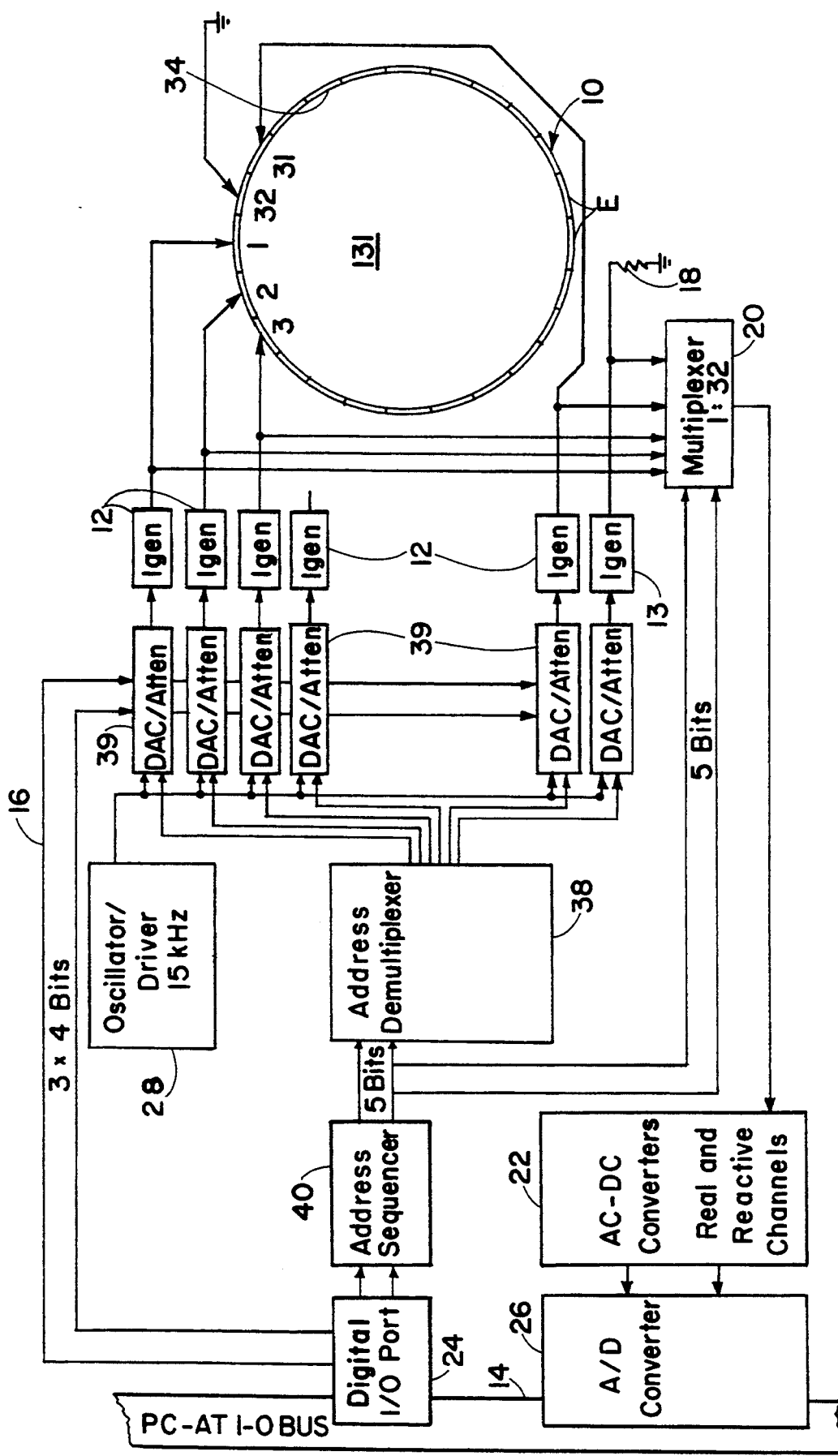
FIG. 2 is a block diagram showing an apparatus which can be used to apply the current patterns and measure the voltages needed to derive information for making impedance images according to the present invention.

FIG. 2, previously disclosed in U.S. Pat. No. 4,920,490, illustrates an apparatus which can be used to practice the invention. The invention consists of an array 10 of 32 uniformly spaced electrodes 1,2, ... 32 in a plane around the inside of an insulating tank 34 of conductive liquid 131, to simulate a human torso. Objects of contrasting conductivity and permittivity may be introduced into the tank to simulate body organs.

The overall system architecture was designed for maximum flexibility with a minimum of special-purpose hardware. The system is an array of thirty-two current generators 12, 13, each of which has a separately programmable output level. A single voltmeter 22 is attached subsequently through a multiplexer 20 to each electrode E of array 10 in tank 34 for measurement purposes. This special-purpose hardware is connected to a microcomputer 14 (e.g. an IBM PC-AT) through a general-purpose analogue and digital interface board 24, 26 (e.g., a Data Translation DT 2800). Synchronization between the instrument and software is accomplished by having the software write clock signals to the digital output port 24. A stable sinusoidal oscillator 28, at 15 kHz is included in the instrument.

The 15 kHz oscillator output is buffered and directed to each of thirty-two current generators 12, 13. Each generator is based upon a three-amplifier configuration, using type LF 412 op-amps. The output of each generation 12, 13 is coupled through a 1 (m$\mu$)F capacitor directly to the output electrode. The maximum load for the current generators is 1,000 ohms at 5 mA rms. With an output current sensing resistor of 432 ohms, the op-amp output voltage ranges between about 2–7 V rms for load resistances between 0 and 1,000 ohms. Input to each current generator is obtained from a multiplying digital-to-analogue converter (DAC) (e.g., an AD 7549), operating as a digitally controlled attenuator 39. The analogue input signal to the DAC reference terminal is the 15 kHz output from the oscillator 28. Digital input to the DAC is obtained from the digital output port 24 of the computer through the DT 2800 board. Some complexity is introduced here since the DAC used requires a sequence of three "nibbles" of four bits each to acquire a full 12 bit word it then converts. This requirement is handled by the controlling software and on-board digital sequencer 40, the DAC circuit is configured as a 4 quadrant converter, so that currents of either polarity and between 0–5 mA rms amplitude may be produced by any of the thirty-two current generators.

One of the electrodes of tank 34 is grounded. For this reason, only thirty-one current generators 12 are actually needed to implement the 32 electrode scheme. The thirty-second current generator 13 is connected to a precision fixed resistor 18, and serves as a reference and test channel.

The digital multiplexer 20 selects one of the 32 electrodes and connects it to the input stage of the voltmeter 22. This meter consists of a two-stage high-pass filter ($f_{co}$–1.9 kHz), followed by a synchronous full-wave demodulator (AD 630). The demodulator is an active switching device synchronized with the oscillator output through an adjustable phase shifter, which compensates for small phase shifts elsewhere in the circuit.

A two-stage low-pass filter having poles or cutoff frequencies of 177 Hz and 1770 Hz then produces a ±5 volt DC signal proportional to the electrode voltage amplitude. This voltage is sampled by the analogue-to-digital convertor (ADC) 26 of the interface board (DT 2801/5716), which has 16 bit resolution, programmable gain, and is under software control. The filter has a calculated attenuation at 24 kHz of 65.0 db, and a calculated ripple of 4 millivolts peak with a 7 volt rms input.

A single digital sequencer 40 addresses both the rent generator 12, 13 and the demultiplexer 20 for the voltmeter 22. Under software control, a master reset signal assures that the sequence begins with channel 1. Sequential counters 38 are then used to address the DAC's 39 as the digital words representing the desired amplitude for each generator are transmitted. When the DAC addressing lines 16 are enabled, new current-specifying words are latched into the DAC's, so that new currents are applied to each electrode E. During the read sequence, when the software does not enable the DAC address line, the counter addresses each channel of the multiplexer 20 in sequence and presents the output of each electrode to the voltmeter 22. The ADC 26 input is then read by the software as the desired input data, with a 15 msec interval allowed between successive electrodes.

The special-purpose hardware is driven by "words" or programs written in FORTH-like language called ASYST (Macmiallan Software Co., Inc.). This interactive, flexible programming language is easily adaptable to the requirements of this hardware and is quickly learned by new programmers. One hardware handler word or program accepts a 32-element array of desired currents, verifies that the array is properly scaled, and sends it to the hardware. As second word recovers and stores a 32-element array containing the electrode voltages.

Connection to the electrode array 10 if through four 76 cm. lengths of 24 conductor strip line, each containing the connections for eight electrodes. Each electrode wire is guarded by the two adjacent wires, which are driven by a buffer amplifier from the current generator circuit. This guarding scheme virtually eliminates the effects of inter-wire capacitances due to the cable.

The current generators were calibrated by introducing a single resistor sequentially to each channel. Gain and offset for each channel were thus separately adjusted in software so that by a table look-up function, differences in the channel-to-channel gains could be reduced from 1% level due to component tolerance to the 1/4096 level achievable by the 12 bit DAC's 39. Similarly, small offsets in the voltmeter circuits were compensated for in software. The variation in current output from the current generators was adjusted to be less than 10 $\mu$A in 5 mA for load changes between one and 800 ohms. The voltmeter multiplexer 20 and A-to-D converter 26 were tested at different read rates. With an interval of 10 msec or greater between successive channels, no influence of one channel on the next was recorded. For faster rates, interactions between successive channels were evident, due to storage in the voltmeter filter. The software therefore drives the voltmeter sequencer with a 15 msec period, so that about ½ second is required to obtain the voltages from all 32 electrodes.

Returning now to FIG. 1, the process of the present invention begins by guessing an initial set of orthogonal current patterns, $j^{(0)}$ and guessing an initial conductivity distribution, $\sigma^{(0)}$. (The most common initial guess is that the distribution of conductivity is uniform throughout. For circular geometry such as shown in FIG. 2, the current patterns guessed would be sines and cosines of increasing spatial frequency.) This step is shown at 200. At this point, 201, k is set to zero signifying the first iteration of the first iterative loop. Also set to zero is n, the number of the iteration of the second iterative loop of the overall process.

Each of the (31 for 32 electrodes) current patterns is applied to the electrodes consecutively, and during its application, the voltages at all electrodes are measured and recorded, shown at 202 in the flow chart. At 203, the theoretical voltage values that would have resulted from the application of the current patterns $j^{(0)}$ to the conductivity distribution guessed is calculated for the particular geometry involved—in this case circular and two-dimensional. In these two steps the symbol R on the flow chart is the matrix of dot products of current and voltage values, experimental in 202 and theoretical in 203.

At 204 a single number $\delta^{(k)}$ called the distinguishability, whose values depend on differences between the measured and calculated voltages. The distinguishability for the set of patterns is the square root of the sums of the squares of the effective difference voltages for each current pattern, which in turn is the square root of the sum of the squares of the difference voltages, those measured minus those calculated, for each electrode of the pattern.

At 205 an entirely new set of current patterns is calculated from the information at hand. First the voltage measurements resulting from each pattern are adjusted to make their average value zero. (The currents injected in each pattern are always set to average zero.) Then the differences between the experimental and calculated values of both voltage and current are normalized by dividing each difference in each pattern by the square root of the sum of the squares of the differences in its pattern. The result is then put into the form of two matrices. One whose columns are the normalized current differences and the other whose columns are the normalized voltage differences. A new matrix is now formed multiplying the voltage difference matrix by the transposed current difference matrix. The eigenvalues and eigenvectors of this matrix may now be determined by standard techniques. The eigenvectors resulting are the normalized values of a new set of current patterns. These may now be multiplied by appropriate factors to set the peak value of current in each pattern to be the same as was used in the first set of patterns. The new set is more nearly optimal for distinguishing the unknown conductivity distribution, given a limit on the peak current value.

At 206 on the flow chart convergence is tested. An overall voltage to current ratio, $\rho$, is calculated for each current pattern by dividing the square root of the sum of the squares of the normalized current differences by the root-mean-square normalized current differences (for the initial current pattern set). Each measured voltage in each pattern then has subtracted from it the product of the appropriate $\rho$ and the newly calculated current value from the second set of patterns. If any one of these differences is larger than any present value, such as twice the smallest increment the voltmeters can read, the test is failed.

If failed, the value of k is updated at 207 and the entire process just described is repeated with the set of current patterns determined in 205 replacing the initial guessed set.

After the number of iterations required to pass the convergence test have ensued, the last set of current patterns is the optimal set (assuming fixed maximum current amplitudes) for distinguishing the unknown distribution of conductivities from the set of conductivity initially guessed. However, it may not be optimal for finding the actual unknown conductivity distribution. To that end we require first a test, 208. The distinguishability calculated in 204 has been maximized by the iteration process. It is likely to be larger than the minimum acceptable value, and a new distribution of conductivities different from that originally guessed must be calculated at 209. These new distributions can be calculated by any of several standard optimization methods.

The second iteration number, n, is updated at 210 and now a full set of the best current patterns at 205 (after the first set of iterations) is applied to the electrodes and the voltages are measured, at 202. At 203 the theoretical voltages are calculated for that set of current patterns but using the updated distribution of conductivities. The process continues with possible further iterations of the first kind until a new set of "best" current patterns have been produced for the updated conductivity distribution. The test 208 is made again. Further updates of conductivities may be needed, each requiring a new "best" set of current patterns until the distinguishability test result at 208 indicates that, within the limits of our measuring ability, we can no longer distinguish the current guess for the conductivity distribution from the actual distribution. This last conductivity distribution calculated is then displayed at to 211 as a two-dimensional variation of conductivity values.

While the specific embodiments of the invention have been shown and described in detail to illustrate the application of the principles of the invention, it will be understood that the invention may be embodied otherwise without departing from such principles.

What is claimed is:

1. In an electrical impedance tomography system that includes a body with an array of electrodes on its surface, a method for finding the values of an unknown distribution of conductivities from which an image may be formed, the method comprising:
 (a) selecting an arbitrary guessed conductivity distribution and applying an arbitrary guessed set of current patterns to the electrodes to generate a voltage pattern on the array for each current pattern;
 (b) measuring all electrode voltages for each current pattern applied;
 (c) calculating values of all theoretical voltages that should have appeared on the electrodes for the body due to the arbitrary set of guessed current patterns and arbitrary guessed conductivity distribution;

(d) calculating a new set of current patterns based on differences between the measured and calculated voltage values;

(e) calculating the differences between electrode currents of the arbitrary set of current patterns and the calculated new set of current patterns, to form current differences;

(f) if any of the current differences are greater than a selected tolerance, applying the new set of current patterns to the electrode array and repeating steps (b) to (e);

(g) when the current differences are smaller than the selected tolerance, considering the new set of current patterns to be an optimal set of spatial current patterns, meaning that the optimal set of spatial current patterns can be used to best distinguish the actual conductivity distribution from that previously assumed, for a fixed limit on peak current values;

(h) testing whether any of the voltage differences between the measured and calculated values at the electrodes, using the optimal current patterns, are larger than a predetermined value;

(i) if so, computing a new conductivity distribution as a function of the new set of current patterns and the measured voltage values;

(j) repeating steps (b) to (g) using the new conductivity distribution to replace the previously assumed distribution in order to find a set of current patterns that better distinguishes the actual conductivity distribution from the new conductivity distribution; and (k) repeating steps (h) to (J) as many times as are necessary to produce a calculated conductivity distribution whose calculated voltages are substantially identical to those measured, from which a conductivity image may be produced.

* * * * *